US011224736B2

(12) United States Patent
Roelle et al.

(10) Patent No.: US 11,224,736 B2
(45) Date of Patent: Jan. 18, 2022

(54) BLOOD PUMP CONTROLLERS

(71) Applicant: TC1 LLC, St. Paul, MN (US)

(72) Inventors: Dustin Roelle, Mountain House, CA (US); Joseph C. Stark, III, San Leandro, CA (US); Ethan Petersen, Oakland, CA (US); Jaime Arturo Romero, San Leandro, CA (US)

(73) Assignee: TC1 LLC, St. Paul, MN (US)

( * ) Notice: Subject to any disclaimer, the term of this patent is extended or adjusted under 35 U.S.C. 154(b) by 230 days.

(21) Appl. No.: 16/425,756

(22) Filed: May 29, 2019

(65) Prior Publication Data

US 2019/0365972 A1 Dec. 5, 2019

Related U.S. Application Data

(60) Provisional application No. 62/678,919, filed on May 31, 2018.

(51) Int. Cl.
*A61M 1/10* (2006.01)
*A61M 60/857* (2021.01)
(Continued)

(52) U.S. Cl.
CPC ........ *A61M 60/857* (2021.01); *A61M 60/205* (2021.01); *A61M 60/50* (2021.01);
(Continued)

(58) Field of Classification Search
CPC ........ A61M 60/148; A61M 2205/8206; A61M 60/871; A61M 60/205; F04B 19/04; H01R 13/5224; H01R 13/5219
See application file for complete search history.

(56) References Cited

U.S. PATENT DOCUMENTS 3,882,861 A    5/1975  Kettering et al.
4,521,871 A    6/1985  Galdun et al.
(Continued)

FOREIGN PATENT DOCUMENTS

DE    19735151 A1    2/1998
EP    1 812 094 A    5/2006
(Continued)

OTHER PUBLICATIONS

"Berlin Heart Incor", My LVAD, Available online at:http://www.mylvad.com/content/berlin-heart-incor, Jul. 16, 2015, 3 pages.
(Continued)

*Primary Examiner* — Jon Eric C Morales
(74) *Attorney, Agent, or Firm* — Kilpatrick Townsend & Stockton LLP

(57) ABSTRACT

An implantable blood pump system is disclosed herein. The implantable blood pump system includes an implantable blood pump and a controller coupled to the blood pump. The controller includes a partially sealed housing defining an internal volume. The controller includes an energy storage component contained within the internal volume and a processor. The processor can generate one or several signals affecting operation of the implantable blood pump. The controller includes a connector receptacle including a plurality of contacts selectively coupled via a circuitry to the energy storage component. The circuitry can electrically couple the plurality of contacts to the energy storage component when a connector insert is received within the connector receptacle and deactivate the plurality of contacts from the energy storage component when the connector insert is not within the connector receptacle.

20 Claims, 4 Drawing Sheets

(51) Int. Cl.
*H01R 13/703* (2006.01)
*A61M 60/50* (2021.01)
*A61M 60/205* (2021.01)

(52) U.S. Cl.
CPC ..... *H01R 13/7036* (2013.01); *A61M 2205/14* (2013.01); *A61M 2205/50* (2013.01); *A61M 2205/8206* (2013.01); *H01R 2201/12* (2013.01)

(56) References Cited

U.S. PATENT DOCUMENTS

| | | | |
|---|---|---|---|
| 5,046,965 | A | 9/1991 | Neese et al. |
| 5,411,534 | A | 5/1995 | Dieken et al. |
| 5,695,471 | A | 12/1997 | Wampler |
| 5,695,474 | A | 12/1997 | Daugherty |
| 5,708,551 | A | 1/1998 | Bosatelli |
| 5,888,242 | A | 3/1999 | Antaki et al. |
| 5,935,105 | A | 8/1999 | Manning et al. |
| 5,991,595 | A | 11/1999 | Romano et al. |
| 6,071,093 | A | 6/2000 | Hart |
| 6,116,862 | A | 9/2000 | Rau et al. |
| 6,146,179 | A | 11/2000 | Denny et al. |
| 6,183,412 | B1 | 2/2001 | Benkowski et al. |
| 6,186,665 | B1 | 2/2001 | Maher et al. |
| 6,234,772 | B1 | 5/2001 | Wampler et al. |
| 6,264,635 | B1 | 7/2001 | Wampler et al. |
| 6,305,962 | B1 | 10/2001 | Maher et al. |
| 6,494,736 | B2 | 12/2002 | Mito |
| 6,592,620 | B1 | 7/2003 | Lancisi et al. |
| 6,688,861 | B2 | 2/2004 | Wampler |
| 6,991,595 | B2 | 1/2006 | Burke et al. |
| 7,340,304 | B2 | 3/2008 | MacDonald et al. |
| 7,425,142 | B1 | 9/2008 | Putz |
| 7,658,613 | B1 | 2/2010 | Griffin et al. |
| 7,699,586 | B2 | 4/2010 | LaRose et al. |
| 7,961,156 | B2 | 6/2011 | Knott et al. |
| 7,976,271 | B2 | 7/2011 | LaRose et al. |
| 7,997,854 | B2 | 8/2011 | LaRose et al. |
| 8,007,254 | B2 | 8/2011 | LaRose et al. |
| 8,029,441 | B2 | 10/2011 | Mazza et al. |
| 8,152,493 | B2 | 4/2012 | LaRose et al. |
| 8,157,720 | B2 | 4/2012 | Marseille et al. |
| 8,186,665 | B2 | 5/2012 | Akema |
| 8,200,335 | B2 | 6/2012 | Donofrio et al. |
| 8,323,174 | B2 | 12/2012 | Jeevanandam et al. |
| 8,344,847 | B2 | 1/2013 | Moberg et al. |
| 8,348,678 | B2 | 1/2013 | Hardisty et al. |
| 8,449,444 | B2 | 5/2013 | Poirier |
| 8,506,471 | B2 | 8/2013 | Bourque |
| 8,562,508 | B2 | 10/2013 | Dague et al. |
| 8,597,350 | B2 | 12/2013 | Rudser et al. |
| 8,628,460 | B2 | 1/2014 | Yomtov et al. |
| 8,639,348 | B2 | 1/2014 | Geheb |
| 8,652,024 | B1 | 2/2014 | Yanai et al. |
| 8,657,733 | B2 | 2/2014 | Ayre et al. |
| 8,668,473 | B2 | 3/2014 | LaRose et al. |
| 8,684,763 | B2 | 4/2014 | Mattson et al. |
| 8,894,561 | B2 | 11/2014 | Callaway et al. |
| 8,971,958 | B2 | 3/2015 | Frikart et al. |
| 9,302,035 | B2 | 4/2016 | Marseille et al. |
| 9,985,374 | B2 | 5/2018 | Hodges |
| 10,124,101 | B2 | 11/2018 | Wong et al. |
| 2002/0007198 | A1 | 1/2002 | Haupert et al. |
| 2005/0071001 | A1 | 3/2005 | Jarvik |
| 2007/0078293 | A1 | 4/2007 | Shambaugh, Jr. et al. |
| 2007/0088249 | A1 | 4/2007 | Duffy et al. |
| 2007/0142696 | A1 | 6/2007 | Crosby et al. |
| 2008/0021394 | A1 | 1/2008 | LaRose et al. |
| 2008/0207042 | A1 | 8/2008 | Schmidt et al. |
| 2009/0118827 | A1 | 5/2009 | Sugiura |
| 2009/0203957 | A1 | 8/2009 | LaRose et al. |
| 2011/0152600 | A1 | 6/2011 | Scott et al. |
| 2011/0160516 | A1 | 6/2011 | Dague et al. |
| 2011/0218383 | A1 | 9/2011 | Broen et al. |
| 2012/0028490 | A1 | 2/2012 | Litzler et al. |
| 2012/0046514 | A1 | 2/2012 | Bourque |
| 2012/0095281 | A1 | 4/2012 | Reichenbach et al. |
| 2012/0172657 | A1 | 7/2012 | Marseille et al. |
| 2012/0183261 | A1 | 7/2012 | Schwandt et al. |
| 2013/0096364 | A1 | 4/2013 | Reichenbach et al. |
| 2013/0121821 | A1 | 5/2013 | Ozaki et al. |
| 2013/0127253 | A1 | 5/2013 | Stark et al. |
| 2013/0170970 | A1 | 7/2013 | Ozaki et al. |
| 2013/0225909 | A1 | 8/2013 | Dormanen et al. |
| 2013/0314047 | A1 | 11/2013 | Eagle et al. |
| 2014/0057463 | A1 | 2/2014 | Bhimavarapu et al. |
| 2014/0073838 | A1 | 3/2014 | Dague et al. |
| 2014/0194985 | A1 | 7/2014 | Vadala, Jr. |
| 2014/0243970 | A1 | 8/2014 | Yanai |
| 2014/0309733 | A1 | 10/2014 | Cotter et al. |
| 2015/0038771 | A1 | 2/2015 | Marseille et al. |
| 2016/0095968 | A1 | 4/2016 | Rudser |
| 2016/0301051 | A1 | 10/2016 | Kubota et al. |
| 2018/0055983 | A1 | 3/2018 | Bourque |
| 2018/0250459 | A1 | 9/2018 | Kimball et al. |
| 2018/0256796 | A1 | 9/2018 | Hansen |
| 2018/0256800 | A1 | 9/2018 | Conyers et al. |
| 2018/0256801 | A1 | 9/2018 | Conyers et al. |
| 2019/0290816 | A1 | 9/2019 | Petersen |
| 2019/0334283 | A1 | 10/2019 | Di Paola et al. |

FOREIGN PATENT DOCUMENTS

| | | |
|---|---|---|
| JP | 01244784 A | 9/1989 |
| WO | 2006055745 A2 | 5/2006 |
| WO | 2010122139 A1 | 10/2010 |
| WO | 2011081626 A1 | 7/2011 |
| WO | 2014107424 A2 | 7/2014 |
| WO | 2015017770 A1 | 2/2015 |
| WO | 2017087380 A1 | 5/2017 |

OTHER PUBLICATIONS

"The HeartMate II System", HeartMate II, Left Ventricular Assist System, Available online at: http://heartmateii.com/heartmate-ii-system.aspx, Jul. 16, 2015, 2 pages.

BLOOD PUMP CONTROLLERS

CROSS REFERENCE TO RELATED APPLICATION DATA

The present application claims the benefit of U.S. Provisional Appln. No. 62/678,919 filed May 31, 2018; the full disclosure of which is incorporated herein by reference in its entirety for all purposes.

BACKGROUND

This application relates generally to mechanical circulatory support systems, and more specifically relates to methods and devices for improved energy efficiency, for an implantable blood pump.

Ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

Operation of a VAD can be controlled and/or affected by a controller communicatingly coupled with the VAD. The controller can be an external controller or an implanted controller. The operation of the controller can be important to the operation of the VAD and can control all or portions of the operation of the VAD including, for example, a speed of the VAD. Some controllers, for example, can monitor one or several parameters relevant to the patient and can affect operation of the VAD according to those one or several monitored parameters. This can include, for example, changing the VAD speed in response to an increase or decrease in physical activity, or the like.

BRIEF SUMMARY

The present disclosure relates to systems and devices for increasing the ruggedization of a controller of a mechanical circulatory support system. The controller can include a housing that can define an internal volume containing an energy storage component. The housing can be sealed and/or partially sealed to prevent water from entering the internal volume of the housing. The housing can include at least one connector receptacle including at least one contact. The at least one contact can be coupled to the energy storage component via circuitry which can detect the connection of the contact with a connector insert and can deactivate and/or activate the at least one contact based on the detected connection status.

One aspect of the present disclosure relates to an implantable blood pump system. The implantable blood pump system includes: an implantable blood pump; and a controller coupled to the blood pump. The controller includes: a partially sealed housing defining an internal volume; an energy storage component contained within the internal volume; and a processor. The processor can operate according to stored instructions to generate one or several signals affecting operation of the implantable blood pump. The controller can include a connector receptacle located in a portion of the housing and including a plurality of contacts selectively coupled via a circuitry to the energy storage component. The circuitry can electrically couple the plurality of contacts to the energy storage component when a connector insert is received within the connector receptacle and deactivate the plurality of contacts from the energy storage component when the connector insert is not within the connector receptacle.

In some embodiments, the partially sealed housing is water-tight and non-air-tight. In some embodiments, the energy storage component can degas during use. In particular embodiments, the housing may be configured to facilitate degassing of the energy storage element during use. This degassing may be the result of a degassing failure mode of the energy storage element. In some embodiments, the connector insert is sealed. In some embodiments, the housing can include multiple pieces joined and partially sealed together to define the internal volume. In some embodiments, the multiple pieces are joined and partially sealed by at least one of: a weld; a gasket; adhesive bonding; potting; or solvent bonding.

In some embodiments, the circuitry selectively coupling the plurality of contacts to the energy storage includes a diode that can deactivate at least one of the plurality of contacts when a mating contact (e.g., of a connector insert) is not mated with the at least one of the plurality of contacts. In some embodiments, the circuitry can detect connection with the connector insert. In some embodiments, the energy storage component can be a battery. In some embodiments, the battery is tolerant of single fault failure. In some embodiments, the battery can be cells arranged in at least two parallel battery packs. In some embodiments, the battery can include four cells arranged in a 2×2S configuration. In some embodiments, the single fault failure can include failure of one of the at least two parallel battery packs.

One aspect of the present disclosure relates to a controller of an implantable medical device. The controller includes: a housing defining an internal volume; an energy storage component; and a processor. In some embodiments, the processor can generate one or several signals affecting operation of the implantable medical device. The controller can include a connector receptacle located in the housing. The connector receptacle can include a plurality of contacts selectively coupled via a circuitry to the energy storage component. In some embodiments, the circuitry can deactivate the plurality of contacts from the energy storage component when mating contacts of a connector insert are not mated to the plurality of contacts of the connector receptacle.

In some embodiments, the housing is at least partially sealed. In some embodiments, the partially sealed housing is water-tight and non-air-tight. In some embodiments, the energy storage component can be a battery. In some embodiments, the battery can be four cells arranged in a 2×2S configuration. In some embodiments, the housing can include multiple pieces joined and partially sealed together to define the internal volume. In some embodiments, the multiple pieces are joined and partially sealed by at least one of: a weld; a gasket; potting; an adhesive bond; or a solvent bond.

In some embodiments, the circuitry selectively coupling the plurality of contacts to the energy storage includes a diode that can deactivate at least one of the plurality of contacts when a mating contact is not mated with the at least one of the plurality of contacts. In some embodiments, the plurality of contacts can include at least one positive contact and at least one negative contact. In some embodiments, the circuitry can detect connection of the at least one negative contact with at least one corresponding mating contact of the connector insert. In some embodiments, the circuitry can deactivate the plurality of contacts when the at least one negative contact is not connected with the at least one corresponding mating contact of the connector insert.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

DETAILED DESCRIPTION

Figure 1:
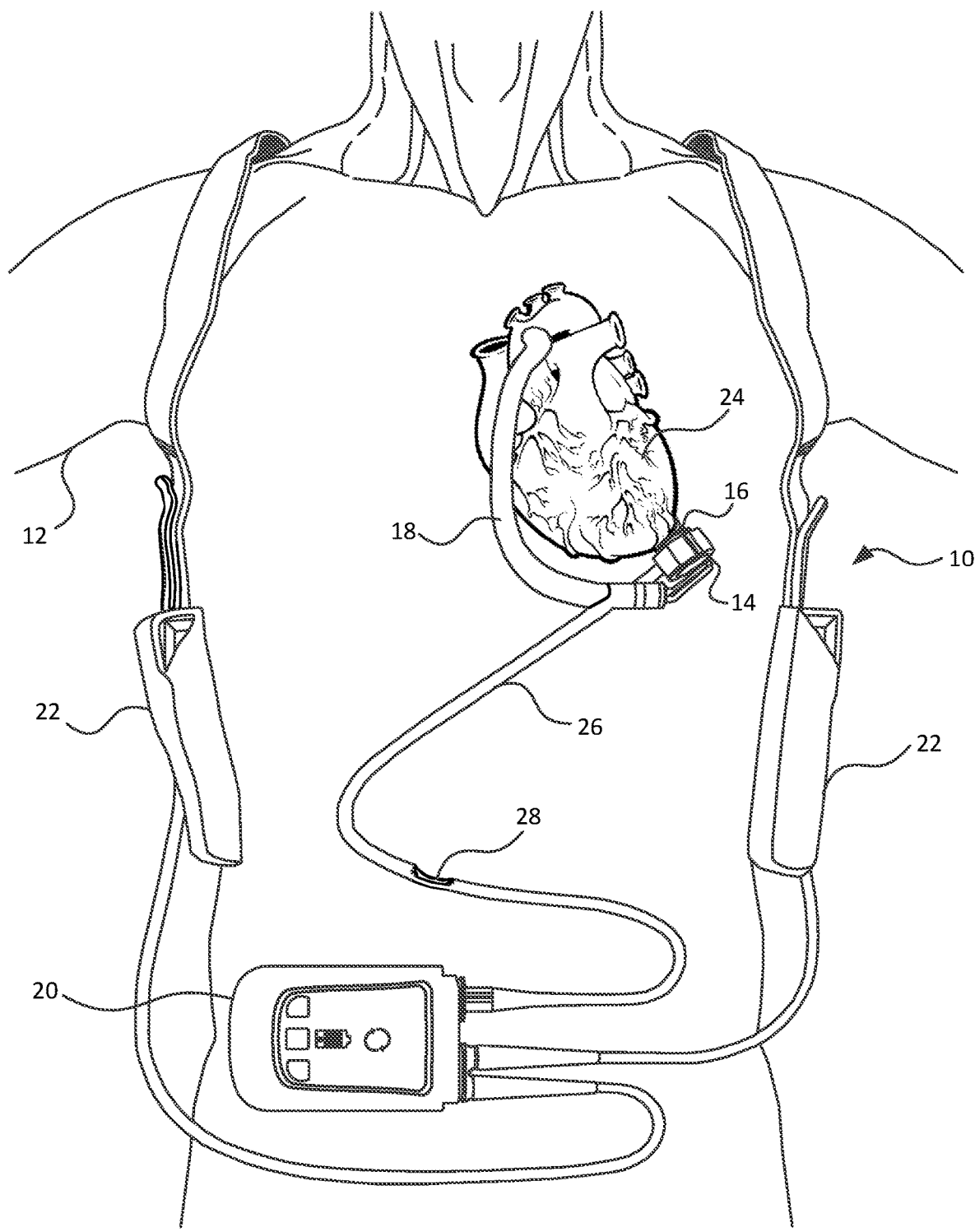
FIG. 1 is an illustration of a mechanical circulatory support system implanted in a patient's body.

Circulatory support systems are increasingly used to support patient's blood circulation. These circulatory systems can include an implantable blood pump such as a VAD and a controller. In some embodiments, the controller can directly control the implantable blood pump via one or several control signals, and/or the controller can provide one or several parameters that can be used by the implantable blood pump to affect operation of the implantable blood pump, such as, for example, to change a speed of the implantable blood pump.

Due to this role of the controller in at least affecting operation of the implantable blood pump, reliability and ruggedness of the controller is important.

This ruggedization of the controller may involve multiple improvements. For example, the ruggedization may involve improvements to the housing of the controller to protect the controller and/or the components of the controller. These improvements to the housing can include, for example, the waterproofing and/or sealing of all or portions of the controller. While all or portions of the controller can be sealed for waterproofing, in some embodiments, this seal is not a hermetic seal, and can allow gas to pass into and out of the controller.

In some embodiments, the ruggedization can include the coupling of circuitry to one or several contacts of one or several connectors of the controller. These one or several connectors can include, for example, one or several connector receptacles and/or connector inserts. In some embodiments, this circuitry can be configured to detect connection of the contacts with mating contacts. In such embodiments, when the contacts are not coupled to mating contacts, the circuitry can deactivate and/or decouple the contacts such that power is not provided to the contacts. The deactivation and/or decoupling of the contacts can prevent the inadvertent delivery of a shock from the contacts, electrical arcing between contacts and/or shorting of contacts, and/or corrosion of the contacts.

The ruggedization can include changes to the batteries and/or energy storage devices within the controller. This can include, for example, the integration of the batteries within the controller. In some embodiments, this integration can be such that battery cells cannot be removed from the controller. This integration of the batteries and the controller can require changes to the controller such that the degassing of the batteries is possible during the charging and/or discharging of the batteries. In some embodiments, the integration of the batteries into the controller can involve the structuring of the battery such that power can be provided by the batteries in the event of failure of one or several of the cells. In some embodiments, this can include structuring batteries, and/or battery cells as parallel power sources. This can include the creation of at least two parallel battery packs. Through these changes to the controller, the controller can be made more rugged and/or robust, and the risk or the effect of failure of all or portions of the controller can be minimized.

With reference now to FIG. 1, an illustration of one embodiment a mechanical circulatory support system 10 implanted in a patient's body 12 is shown. The mechanical circulatory support system 10 comprises an implantable blood pump 14, ventricular cuff 16, outflow cannula 18, system controller 20, and external power sources 22. The implantable blood pump 14 may comprise a VAD that is attached to an apex of the left ventricle, as illustrated, or the right ventricle, or both ventricles of the heart 24. The VAD may comprise a centrifugal (as shown) or axial flow pump as described in further detail herein that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety.

The blood pump 14 may be attached to the heart 24 via the ventricular cuff 16 which is sewn to the heart 24 and coupled to the blood pump 14. The other end of the blood pump 14 connects to the ascending aorta via the outflow cannula 18 so that the VAD effectively diverts blood from the weakened ventricle and propels it to the aorta for circulation to the rest of the patient's vascular system.

In FIG. 1, the mechanical circulatory support system 10 is illustrated in the configuration in which powered operation is enabled via external power source 22. A driveline 26 which exits through the patient's abdomen 28, connects the implanted blood pump 14 to the system controller 20, which monitors system 10 operation. Related controller systems applicable to the present invention are described in greater detail below and in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety.

The system may be powered by either one, two, or more external power sources 22. In some embodiments, one or several energy storage components, such as, for example, one or several batteries, in the controller 20 can power the mechanical circulatory support system 10. It will be appreciated that although the system controller 20 and power source 22 are illustrated outside/external to the patient body, the driveline 26, system controller 20 and/or power source 22 may be partially or fully implantable within the patient, as separate components or integrated with the blood bump 14. In some embodiments, for example, the system controller 20 can be implanted within the patient's body, and can receive power from a power source 22 that can be external to the patient's body. In some embodiments, this power can be provided to the controller 20 via a wired or wireless connection between the controller 20 and the power source 22. In some embodiments, this wireless connection can comprise a transcutaneous energy transfer system (TETS) that can, for example, include one or several resonant circuits. Examples of such modifications are further described in U.S. Pat. No. 8,562,508 and U.S. Patent Publication No. 2013/0127253, all of which are incorporated herein by reference for all purposes in their entirety.

Figure 2:
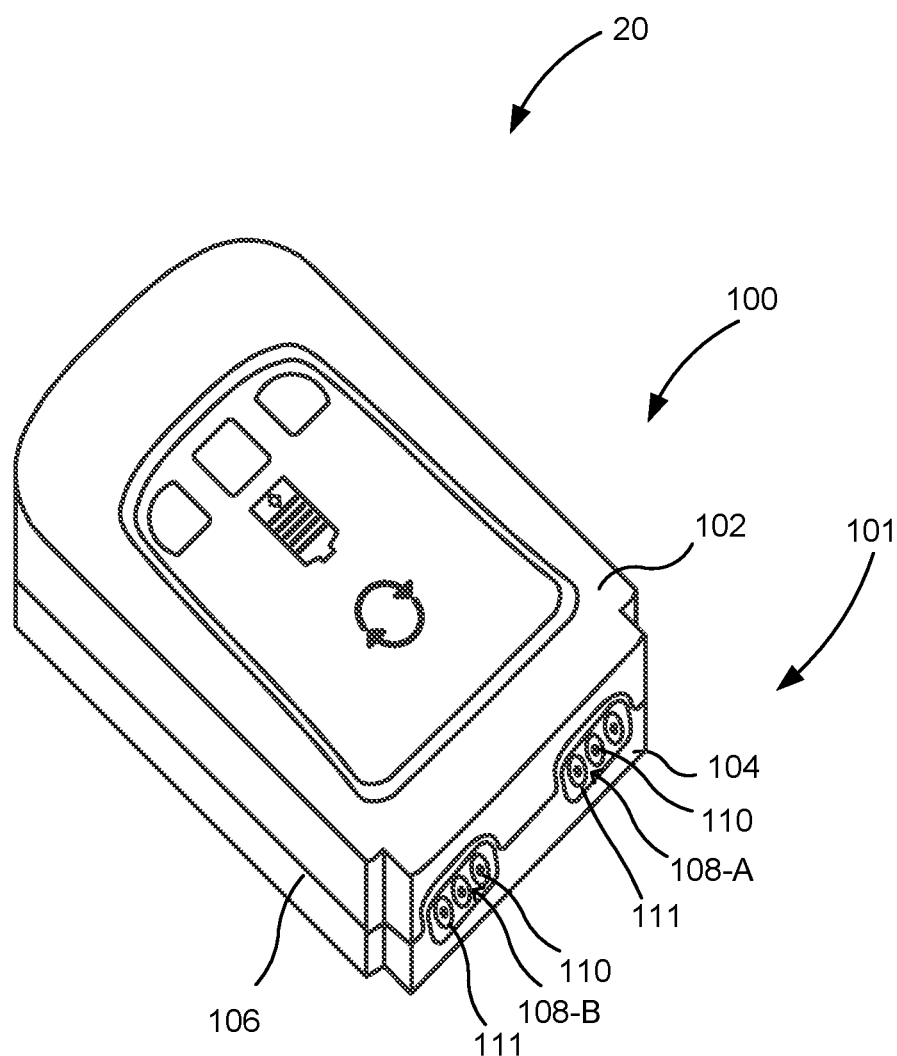
FIG. 2 is a perspective view of one embodiment of the system controller.

With reference now to FIG. 2, a perspective view of one embodiment of the system controller 20 is shown. The system controller 20 can be coupled to the blood pump 14, and can specifically be communicatively coupled to the blood pump 14. The system controller 20 can comprise a housing 100, that can define an internal volume. In some embodiments, the housing 100 can comprise a sealed housing 100 and/or a partially sealed housing 100. In some embodiments, the housing 100 can be sealed in a watertight manner so that water cannot enter into the internal volume, and/or in some embodiments, the housing 100 can be sealed in a non-airtight manner so as to allow gas to exit the housing 100, such as, for example, can occur after degassing of energy storage components, such as one or several batteries contained within the housing 100.

In some embodiments, the housing 100 can comprise a plurality of pieces 101 joined and/or sealed together to define the internal volume of the housing. As depicted in FIG. 2, these pieces 101 can include at least a first piece 102 and a second piece 104. These pieces can be connected by a sealed joint 106, also referred to herein as a joint 106 and/or as a seal 106. In some embodiments, the sealed joint 106 can comprise at least one of the weld, a gasket, an adhesive bond, a solvent bond, or the like. In some embodiments, these pieces 101, and/or the sealed joint 106 can be watertight, and in some embodiments, these pieces 101 and/or the sealed joint 106 can be watertight and non-airtight.

The housing 100 can comprise features configured to couple the controller 20 with other components of the mechanical circulatory support system 10. In some embodiments, these features can comprise one or several connector receptacles 108 located in a portion of the housing 100 and the connector receptacles 108 can each include one or several contacts 110, which one or several contacts can include, in some embodiments, at least one positive contact and at least one negative contact. In some embodiments, the one or several contacts can comprise an electrically conductive material such as a metal, a metal alloy, or the like. This can include, for example, a gold alloy, a silver alloy, an aluminum alloy, a steel alloy, a platinum alloy, and/or a palladium alloy.

In some embodiments, each of the contacts 110 can be surrounded by a dielectric 111, where the dielectric 111 can be, for example, hydrophobic. In some embodiments, the dielectric 111 can seal with the mating connector of the connector insert. This seal can prevent the expelling of any ingress such as, for example, water from between contacts, and can prevent the return of any ingress after the contacts are mated. In some alternate embodiments, the seal can facilitate the expelling of, for example, water from between contacts. In some embodiments, the dielectric 111 and/or the contacts 110 can be designed to withstand initial arcing and/or to minimize initial arcing.

The connector receptacles 108 can be configured to receive one or several connector inserts to allow connection of the controller 20 with, for example, the blood pump 14 and/or the external power source 22. These connector receptacles 108 can include a first connector receptacle 108-A that can receive a connector insert coupling the controller 20 to, for example, the external power source 22 and a second connector receptacle 108-B that can receive a connector insert coupling, for example, the controller 20 to the blood pump 14 via, for example, the driveline 26. In some embodiments, the one or several connector receptacles 108 can be sealed so as to be watertight and/or can be sealed to be watertight and non-airtight. Similarly, in some embodiments, the connector insert for connecting with the connector receptacle can be sealed.

Figure 3:
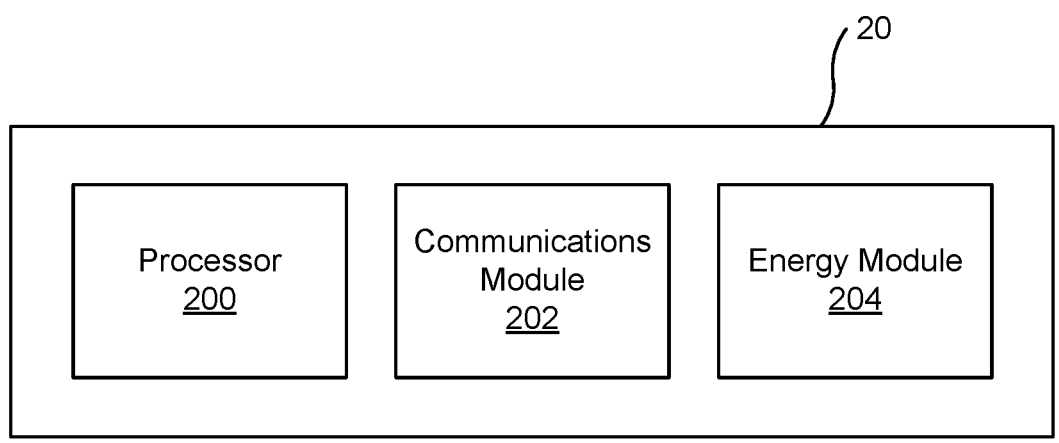
FIG. 3 is a schematic illustration of one embodiment of the controller.

With reference now to FIG. 3, a schematic illustration of one embodiment of the controller 20 is shown. The controller 20 can include at least one processor 200. In some embodiments, the processor 200 can provide instructions to and receive information from the other components of the mechanical circulatory support system 10. This can include, for example, generating one or several signals affecting operation of the implantable blood pump 14. The processor 200 can act according to stored instructions, which stored instructions can be located in a memory associated with the processor 200, and/or in other components of the mechanical circulatory support system 10. The memory can comprise, in some embodiments, volatile memory, non-volatile memory, EEPROM, FLASH, or the like. The processor 200 can, in accordance with stored instructions, make decisions. The processor 200 can comprise a microprocessor, such as a microprocessor from Intel® or Advanced Micro Devices, Inc.®, ST Micro®, or the like.

In some embodiments, the stored instructions directing the operation of the processor 200 may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

The controller 20 can include a communications module 202. The communications module 202 can send information to, and receive information from other components of the mechanical circulatory support system 10. In some embodiments, for example, the communications module 202 can send information to and/or receive information from the implantable blood pump 14 and/or the external power source. In some embodiments, the communications module 202 can send one or several signals generated by the processor 200 and affecting operation of the implantable blood pump 14 to the implantable blood pump 14. In some embodiments, the communications module 202 can further communicate information with one or several monitors, and/or one or several patient computing devices such as smart phones, tablets, PCs, laptops, or the like. The communications module 202 can be configured to wired or wirelessly communicate.

The controller 20 can include an energy module 204. The energy module 204 can receive power from, for example, the external power source 22, and/or provide power to the implantable blood pump 14. The energy module 204 can comprise one or several energy storage components and associated circuitry. The energy module 204 and specifically the one or several energy storage components of an associated circuitry can be located within the internal volume of the housing 100 of the controller 20. In some embodiments, the one or several energy storage components can be capable of degassing when the one or several energy storage components are charged or discharged.

The one or several energy storage components can comprise, for example, one or several batteries, and/or one or several batteries cells. The energy storage components can be connected to the connector receptacles 108 via circuitry that can, in some embodiments, electrically couple and/or activate one or several of the contacts 110 of the connector receptacle 108 which the energy storage component is connected when a connector insert is received within the connector receptacle 108. In some embodiments, the circuitry can deactivate and/or electrically decouple the one or several contacts 110 of the connector receptacle 108 when the connector insert is not received within the connector receptacle 108.

Figure 4:
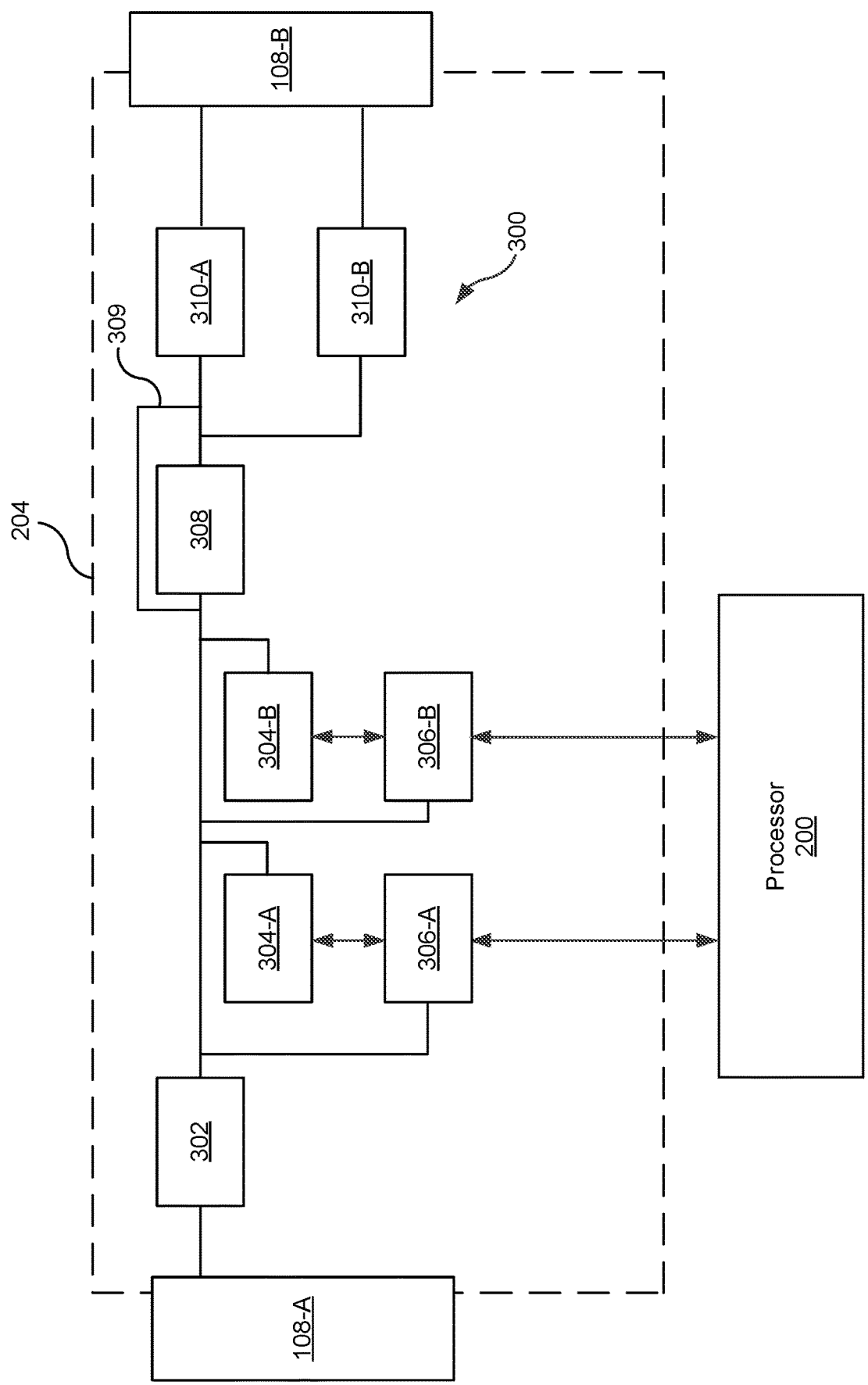
FIG. 4 is a detailed view of one embodiment of an energy module of the controller.

With reference now to FIG. 4, a detailed view of one embodiment of the energy module 204 is shown. The energy module can include the first connector receptacle 108-A and the second connector receptacle 108-B. The first connector receptacle 108-A can be coupled with an input protection module 302 that can include, for example, a diode. In some embodiments, the input protection module can be configured to protect the energy module 204 from a reverse polarity connection via a diode which can be an ideal diode. In some embodiments, the input protection module 302 can further include circuitry configured to detect a presence of a connector insert within the first connector receptacle 108-A and/or connection of one or several contacts of the first connector receptacle 108-A with one or several contacts of the connector insert. In some embodiments, for example, the circuitry can be configured to detect connection of the at least one negative contact with at least one corresponding mating contact of the connector insert. In some embodiments, when the presence of a connector insert is not detected, one or several contacts in the first connector receptacle 108-A can be deactivated and/or electrically decoupled from the one or several energy storage components of the energy module 204. In some embodiments, the circuitry can be configured to deactivate the plurality of contacts when the at least one negative contact is not connected with the at least one corresponding mating contact of the connector insert. In some embodiments, for example, this circuitry can comprise a diode that can deactivate at least one of the plurality of contacts when a mating contact is not mated with the at least one of the plurality of contacts, and/or that can deactivate at least one of the plurality of contacts when a connector insert is not received within the first connector receptacle 108-A.

The energy module 204 can comprise one or several energy storage components 304, and specifically can include at least a first energy storage component 304-A and a second energy storage component 304-B. In some embodiments, these energy storage components 304 can be contained in a serviceably compartment of the housing 100 to allow replacement of the energy storage components 304, and in some embodiments, these energy storage components 304 can be contained in a non-serviceable compartment of the housing 100 of the controller 20.

These energy storage components 304 can, in some embodiments, comprise rechargeable energy storage components 304. In some embodiments, the one or several energy storage components 304 can comprise one or several batteries and/or one or several battery cells. These batteries and/or battery cells can comprise any desired battery type or chemistry and/or cell type. In some embodiments, for example, the cells can comprise prismatic, pouch, and/or cylindrical cells. In some embodiments, the batteries can comprise one or several Lithium Ion 18650 batteries.

In some embodiments, these one or several energy storage components can be arranged and/or have an architecture to be tolerant of single fault failure. Specifically, in some embodiments, in the event that one or several energy storage components fails, energy can still be provided to the implantable blood pump 14. This can be achieved, in some embodiments, via the arranging one or several batteries and/or one or several battery cells in parallel.

In some embodiments, these one or several batteries can be arranged in one or several battery packs. In some embodiments, a plurality of batteries can be arranged in at least two battery packs, at least one of which can be in parallel with another of the at least two battery packs. In such an embodiment, a single fault failure can comprise failure of one of the parallel battery packs. In some embodiments, the battery can comprise four cells arranged in a 2×2S configuration that include two parallel battery packs, each of which battery packs includes two cells in series.

As depicted in FIG. 4, the energy storage components can be coupled with a management circuit 306. The management circuit 306 can additionally be coupled to the processor 200. In some embodiments, each of the plurality of energy storage components can be coupled to an independent management circuit 306. In such an embodiment, the first energy storage component 304-A can be coupled to a first management circuit 306-A and the second energy storage component 304-B can be coupled to a second management circuit 306-B. In some embodiments, the management circuit 306 can control the output of the associated energy storage component 304 to maximize life of the energy storage component, manage the discharge of the energy storage component 304, monitor health of the battery storage component 304, or the like. In some embodiments, the monitoring of the health of the battery storage component 304 can include monitoring of the addition life of the battery storage component 304 and/or the providing of a replacement recommendation and/or maintenance recommendation when the life of the battery storage component 304 drops below a threshold value.

The battery storage components can be coupled to a power converter 308 and/or transformer that can: step up voltage, step down voltage, step up current, and/or step down current. In some embodiments, the power converter 308 can comprise a boost converter that can step up the voltage from the batteries to a voltage for providing to the implantable blood pump 14. In some embodiments, an alternative path 309 can extend around the power converter 308. This alternative path 309 can include a diode which can direct current through the power converter 308 when the voltage is not above a threshold value and can bypass the power converter 308 when the voltage is above a threshold value.

The energy module 204 includes at least one output protection module 310, and as depicted in FIG. 4, can include a first output protection module 310-A and a second output protection module 310-B. The output protection modules 310 can be configured to protect the implantable blood pump 14 from high output voltages that could damage the blood pump 14.

In some embodiments, the output protection module 310 can further include circuitry configured to detect a presence of a connector insert within the second connector receptacle 108-B and/or connection of one or several contacts of the second connector receptacle 108-B with one or several contacts of the connector insert.

In some embodiments, for example, the circuitry can be configured to detect connection of the at least one negative contact with at least one corresponding mating contact of the connector insert. In some embodiments, when the presence of a connector insert is not detected, one or several contacts in the second connector receptacle 108-B can be deactivated and/or electrically decoupled from the one or several energy storage components of the energy module 204. In some embodiments, the circuitry can be configured to deactivate the plurality of contacts when the at least one negative contact is not connected with the at least one corresponding mating contact of the connector insert. In some embodiments, for example, this circuitry can comprise a diode that can deactivate at least one of the plurality of contacts when a mating contact is not mated with the at least one of the plurality of contacts, and/or that can deactivate at least one of the plurality of contacts when a connector insert is not received within the second connector receptacle 108-B.

In some embodiments, the output circuitry can comprise a plurality of logic components that can be configured to detect connection of contacts within the receptacle connector 108-B and the connector insert. In some embodiments, this circuitry can be powered by a low-current voltage derived directly from the energy storage components. In some embodiments, detection of connection can be determined based on return of a voltage signal through from the connector insert. When this voltage signal is connected to the connection detection circuitry, a logic component linked with the returned voltage signal can, in some embodiments, be pulled low, which can be used to indicate connection and to activate contacts at the second receptacle connector 108-B.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. An implantable blood pump system comprising:
an implantable blood pump; and
a controller coupled to the implantable blood pump, the controller comprising:
 a partially sealed housing defining an internal volume;
 an energy storage component contained within the internal volume;
 a processor configured to generate one or several signals affecting operation of the implantable blood pump; and
 a connector receptacle located in a portion of the housing and comprising a plurality of contacts selectively coupled via a circuitry to the energy storage component, wherein the circuitry is configured to electrically couple the plurality of contacts to the energy storage component when a connector insert is received within the connector receptacle and wherein the circuitry comprises a diode configured to deactivate at least one of the plurality of contacts from the energy storage component when a mating contact of the connector insert is not mated with the at least one of the plurality of contacts of the connector receptacle.

2. The system of claim 1, wherein the partially sealed housing is water-tight and non-air-tight.

3. The system of claim 2, wherein the partially sealed housing is configured to facilitate degassing of the energy storage component during a degassing failure mode when in use.

4. The system of claim 2, wherein the connector insert is sealed.

5. The system of claim 1, wherein the housing comprises multiple pieces joined and partially sealed together to define the internal volume.

6. The system of claim 5, wherein the multiple pieces are joined and partially sealed by at least one of: a weld; a gasket; adhesive bonding; or solvent bonding.

7. The system of claim 1, wherein the circuitry is configured to detect connection with the connector insert.

8. The system of claim 1, wherein the controller further comprises at least one output protection module configured to protect the implantable blood pump from high output voltages.

9. The system of claim 1, wherein the controller further comprises a management circuit configured to at least one of monitor the energy storage component, control output of the energy storage component, or maximize life of the energy storage component.

10. The system of claim 1, wherein the energy storage component comprises a battery, wherein the battery comprises four cells arranged in a 2×2S configuration.

11. A controller of an implantable medical device, the controller comprising:
a housing defining an internal volume;
an energy storage component;
a processor configured to generate one or several signals affecting operation of the implantable medical device; and
a connector receptacle located in the housing and comprising a plurality of contacts selectively coupled via a circuitry to the energy storage component, wherein the circuitry is configured to deactivate the plurality of contacts from the energy storage component when mating contacts of a connector insert are not mated to the plurality of contacts of the connector receptacle, wherein the plurality of contacts comprises at least one positive contact and at least one negative contact, wherein the circuitry is configured to detect connection of the at least one negative contact with at least one corresponding mating contact of the connector insert, and wherein the circuitry is configured to deactivate the plurality of contacts when the at least one negative contact is not connected with the at least one corresponding mating contact of the connector insert.

12. The controller of claim 11, wherein the housing is at least partially sealed.

13. The controller of claim 12, wherein the partially sealed housing is water-tight and non-air-tight.

14. The controller of claim 13, wherein the energy storage component comprises a battery.

15. The controller of claim 14, wherein the battery comprises four cells arranged in a 2×2S configuration.

16. The system of claim 11, wherein the circuitry selectively coupling the plurality of contacts to the energy storage component comprises a diode configured to deactivate at least one of the plurality of contacts when a mating contact of the connector insert is not mated with the at least one of the plurality of contacts.

17. An implantable blood pump system comprising:
an implantable blood pump; and
a controller coupled to the implantable blood pump, the controller comprising:
a partially sealed housing defining an internal volume;
an energy storage component contained within the internal volume, wherein the energy storage component comprises a battery tolerant of a single fault failure, wherein the battery comprises four cells arranged in two parallel battery packs in a 2×2S configuration;
a processor configured to generate one or several signals affecting operation of the implantable blood pump; and
a connector receptacle located in a portion of the housing and comprising a plurality of contacts selectively coupled via a circuitry to the energy storage component, wherein the circuitry is configured to electrically couple the plurality of contacts to the energy storage component when a connector insert is received within the connector receptacle and deactivate the plurality of contacts from the energy storage component when the connector insert is not within the connector receptacle.

18. The system of claim 17, wherein the single fault failure comprises failure of one of the two parallel battery packs.

19. The controller of claim 17, wherein the circuitry selectively coupling the plurality of contacts to the energy storage component comprises a diode configured to deactivate at least one of the plurality of contacts when a mating contact is not mated with the at least one of the plurality of contacts.

20. A controller of an implantable medical device, the controller comprising:
a housing defining an internal volume, wherein the housing is at least partially sealed and comprises multiple pieces joined and partially sealed together to define the internal volume, and wherein the multiple pieces are joined and partially sealed by at least one of: a weld; a gasket; an adhesive bond; or a solvent bond an energy storage component;

a processor configured to generate one or several signals affecting operation of the implantable medical device; and a connector receptacle located in the housing and comprising a plurality of contacts selectively coupled via a circuitry to the energy storage component, wherein the circuitry is configured to deactivate the plurality of contacts from the energy storage component when mating contacts of a connector insert are not mated to the plurality of contacts of the connector receptacle.

* * * * *